United States Patent [19]
Hsu

[11] Patent Number: 6,143,547
[45] Date of Patent: Nov. 7, 2000

[54] CELL LINE DERIVED FROM *PENAEUS MONODON* AND A METHOD OF GROWING VIRUS USING THE SAME

[75] Inventor: Ya-Li Hsu, Taipei, Taiwan

[73] Assignee: Academia Sinica, Taipei, Taiwan

[21] Appl. No.: 09/323,093

[22] Filed: Jun. 1, 1999

Related U.S. Application Data

[60] Provisional application No. 60/122,401, Mar. 2, 1999.

[51] Int. Cl.[7] ............................. C12N 7/00; C12N 5/06
[52] U.S. Cl. ..................................... 435/235.1; 435/325
[58] Field of Search .......................... 435/5, 7.21, 235.1, 435/325

[56] References Cited

U.S. PATENT DOCUMENTS 5,236,840   8/1993   Loh et al. ............................. 435/235.1

OTHER PUBLICATIONS

Ya–li–Hsu, et al. "Developmnt of an in vitro subculture system for the oka organ (Lymphoid tissue) of *Penaeus monodon*", Aquaculture, 136 (1995) 43–55.

Ya–li Hsu, et al. "Development of an In Vitro Subculture System for Prawn Tissues", Proceedings of the International Symposium on Biotechnology Applications in Aquaculture Asian Fisheries Society Special Publication No. 10, pp. 161–170, 1995.

Flegel, T.W.; Major viral diseases of the black tiger prawn (*Penaeus monodon*) in Thailand. World Journal of Microbiology & Biotechnology (1997) vol. 13, No. 4, pp. 4–33–442.

*Primary Examiner*—Donna C. Wortman
*Assistant Examiner*—Robert A. Zeman
*Attorney, Agent, or Firm*—Fei-Fei Chao; Venable, Baetjer, Howard & Civiletti, LLP

[57]   ABSTRACT

The present invention relates to the establishment of an immortal shrimp cell line (PMO) derived from Penaeus monodon. This cell line is susceptible to and capable of mass producing virus, which includes, but not limited to, white spot syndrome virus (WSSV), Panaeus monodon baculovirus (MBV), infectious hypodermal and hematopoietic necrosis virus (IHHNV), and infectious pancreatic necrosis virus (IPNV). This invention also relates to the method of mass producing virus using PMO as a host.

5 Claims, 9 Drawing Sheets

CELL LINE DERIVED FROM *PENAEUS MONODON* AND A METHOD OF GROWING VIRUS USING THE SAME

RELATED APPLICATION

This application claims the priority of U.S. Provisional Application Ser. No. 60/122,401, filed on Mar. 2, 1999, which is incorporated herein by reference.

FIELD OF THE INVENTION

The present invention relates to an immortal cell line (PMO) derived from the Oka organ (lymphoid tissue) of the Penaeus monodon. The PMO is susceptible to and can mass produce virus, particularly shrimp virus [e.g., white spot syndrome virus (WSSV), monodon baculovirus (MBV), and infectious hypodermal hematopoietic necrosis virus (IHHNV)], or other fish and shellfish virus [e.g., infectious pancreatic necrosis virus (IPNV)] in vitro. The present invention also relates to a method for growing virus in PMO cells.

BACKGROUND OF THE INVENTION

Since the technology breakthroughs in the artificial fertilization field, culturing crustaceans using mass seed production and feed formulation techniques have rapidly turned the crustacean culture industry into one of the world's most commercially important business. Among the variety of crustaceans, shrimp, particularly penaeid shrimp, has become number one cultivated crustacean in southeast Asia, especially in Taiwan.

In recent years, the penaeid shrimp of southeast Asia are severely threatened by viral infections. According to recent reports, four baculoviruses, namely, white spot syndrome virus (WSSV), Penaeus monodon baculovirus (MBV), baculoviral midgut gland necrosis (BMN), and baculovirus penaei (BP), have been identified as the contributing pathogens which cause the high mortality in penaeid shrimps in southeast Asia.

Viral diseases cannot be cured by therapeutic reagents. The best ways to control the diseases include prevention through early detection and development of vaccines. In either way, the understanding of the biological, biochemical, and serological characteristics of the viruses is fundamentally required, which in turn requires the industry to have the capacity of mass producing the viruses, preferably through an in vitro cell culture system. So far, due to the lack of susceptible penaeid shrimp cell culture system, research on penaeid viruses has been limited to histopathological and transmission electron microscopic observation only. Therefore, the development of a new culture system which can be susceptible to WSSV, MBV, BMN, and/or BP is desperately in demand in order to control the wide spread of viral diseases in penaeid shrimps.

In 1990, an established fish cell line, epithelioma papillosum cyprini (EPC) originating from the carp, was reported. This cell line was found to be susceptible to the shrimp infectious hypodermal and hematopoietic necrosis virus (IHHNV) (U.S. Pat. No. 5,236,840). The establishment of EPC leads to the subsequent findings of cures for IHHNV. Unfortunately, EPC is not susceptible to WSSV, MBV, BMN, or BP.

Since then, there have been several other attempts by researchers to extend the culture life span of penaeid shrimp primary cell cultures. Unfortunately, none has successfully passed the cells beyond the primary stage.

In 1995, two reports describing the development of an in vitro subculture system using cells from the oka organ of Penaeus monodon were published (See Hsu et al. (1995), *Aquaculture*, 136:43–55, and Hsu et al. (1995), *Proc. Internatl. Symposium on Biotech. Appl. in Aquaculture*, 10:161–170, which are herein incorporated by reference). These two reports were authored by the same inventor as in the present invention. The cells from the reported subculture system had been maintained for more than 90 passages. The reports also showed that after 60 passages, the morphology of these cells changed from suspended cells to monolayers, which served as an early indication of the establishment of a cell line. However, the reports not only did not provide information as to the genetic and biochemical characteristics of the cell line, but also were silent on the susceptibility or mass production capability of the cell line to virus, especially shrimp virus and other fish or shellfish virus.

In the invention to be presented in the following sections, an establishment of an immortal cell line (PMO) will be introduced. This immortal cell line is developed from the cells described in the previous reports (id.) by passing the cells to more than 150 passages. Experimental results which show that the PMO cell line is susceptible to various shrimp, fish, and shellfish viruses, and has the capability of mass producing the viruses will also be described. The mass production of viruses using this PMO cell line provides resources for future studies on viral gene functions, virus-host cell interactions, and signal transductions after viral infection. Finally, because the PMO cells are derived from lymphoid organ, they may provide an experimental model for the future studies of the cellular and humoral immunity of shrimp.

SUMMARY OF THE INVENTION

The first embodiment of the present invention provides for an immortal cell line (PMO) which is derived from the Oka organ (lymphoid tissue) of the Penaeus monodon. PMO is susceptible to and can mass produce viruses, particularly shrimp virus [such as, but not limited to, white spot baculovirus (WSSV), Penaeus monodon baculovirus (MBV), and infectious hypodermal and hematopoietic necrosis virus (IHHNV)] and fish or shellfish virus [such as, but not limited to, infectious pancreatic necrosis virus (IPNV)].

The second embodiment of the present invention provides for an in vitro method of growing virus using PMO as host cells. The susceptibility of the virus in PMO cells can be observed by cytopathology effect (CPE). The method for growing the virus comprises the steps of: (1) introducing said virus into PMO cells; (2) incubating PMO cells in a nutrient medium suitable for growth and replication of the virus; and (3) harvest the virus from the PMO cell culture. The harvesting procedures comprises the steps of: (1) forming a virus-containing cell homogenate containing in a buffer; (2) centrifuging the homogenate to remove the cell debris and collecting a supernatant; (3) layering said supernatant on a gradient (preferably a sucrose gradient; more preferably a 36–65% (W/W) sucrose gradient); (4) centrifuging the gradient till an isopycnic condition is reached; and (5) collecting the virus from a visible viral band on the gradient.

DETAILED DESCRIPTION OF THE INVENTION

In accordance with the first embodiment of the present invention, there is provided for an immortal cell line (PMO) which is derived from the Oka organ tissue of Peneaus monodon. A vital sample of this cell line was deposited at the China Center for Type Culture Collection (CCTCC), Wuhen University, Wuhen, P. R. China before the issuance of the patent, under the provisions of the Budapest Treaty for the International Recognition of the Deposit of Microorganisms for the Purpose of Patent Procedure. The assigned deposit number for this cell line is CCTCC deposit No. C 200004.

The experimental designs and results relating to the establishment of the PMO cell line are illustrated, but not limited to, in the following examples:

EXAMPLE 1
Establishment of PMO Cell line

The PMO cell line was established as follows: Cells (approximately $3 \times 10^5$ cells were seeded in each 25 cm$^2$ flask) from the Oka organ tissue of grass prawns were cultured and subcultured in Leibovitz's L-15 medium supplemented with 100 IU/ml penicillin, 100 μg/ml streptomycin, 1.25 μg/ml fungizone and 10% fetal calf serum and incubated at 28° C. The cells were subcultured at an interval ranging between 3 and 5 days. The optimal culture conditions were measured according to the growth rate, which was obtained from counting cultured cells every 24 hrs for 7 days with a hemocytometer.

EXAMPLE 2
Optimization of the Growth Conditions For PMO cells

To study the optimal conditions of the PMO cell line, PMO cells were seeded in 25 cm$^2$ flasks with about $3 \times 10^5$ cells each, and cultured in L-15 medium supplemented with various concentrations of serum, NaCl, or bFGF at various temperatures. The optimal culture conditions of PMO cells were determined by the growth rate which was measured by counting cultured cells every 24 hours for 7 days using a hemocytometer.

Figure 1:
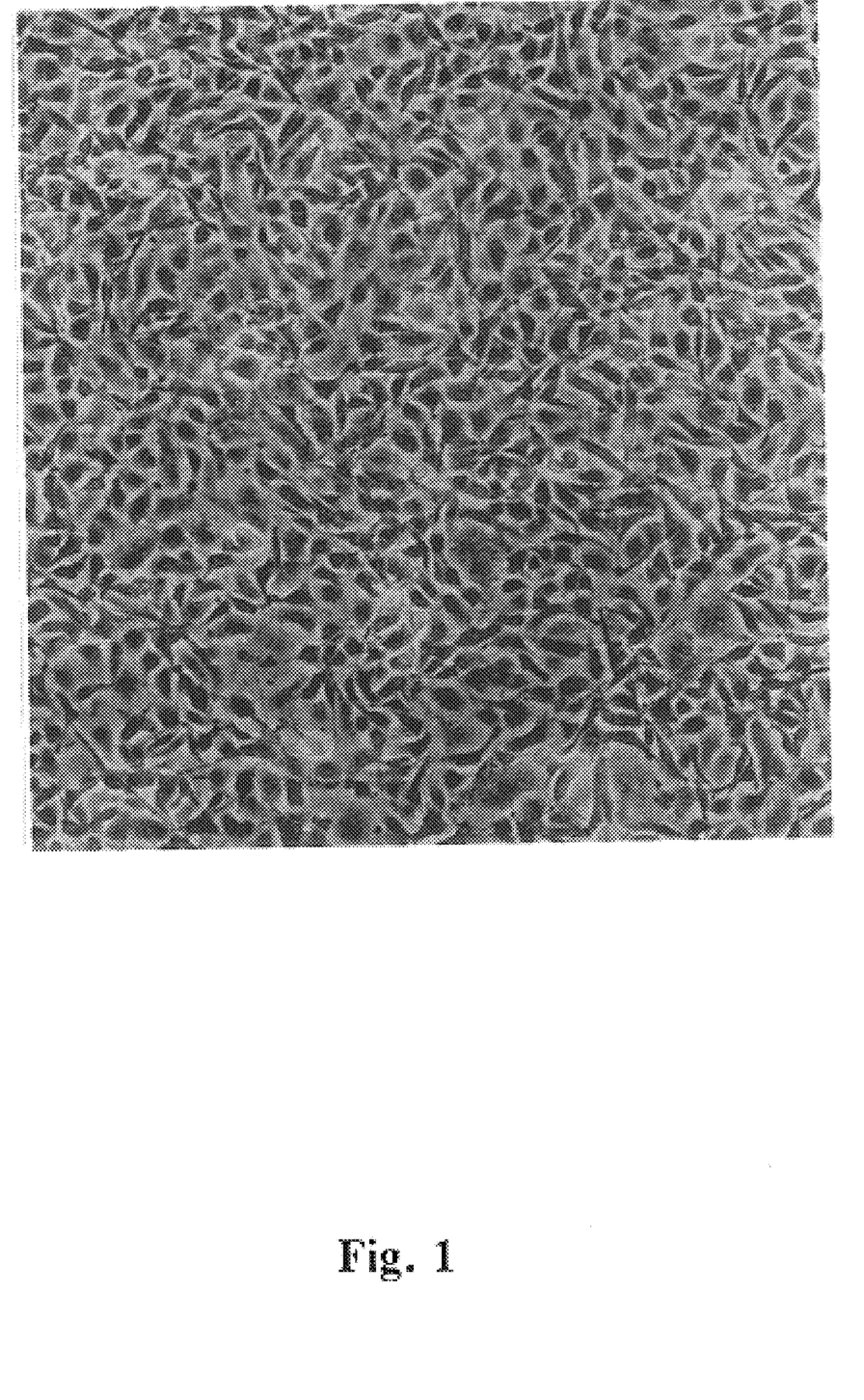
FIG. 1 is a light microscopic picture of the PMO cells after 150 passage which show fibroblast and epithelial morphologies.

As shown in FIG. 1, for PMO cell culture which has been splitted for more than 150 passages, most of the PMO cells are transformed into adhesive fibroblast-like cells.

Figure 2:
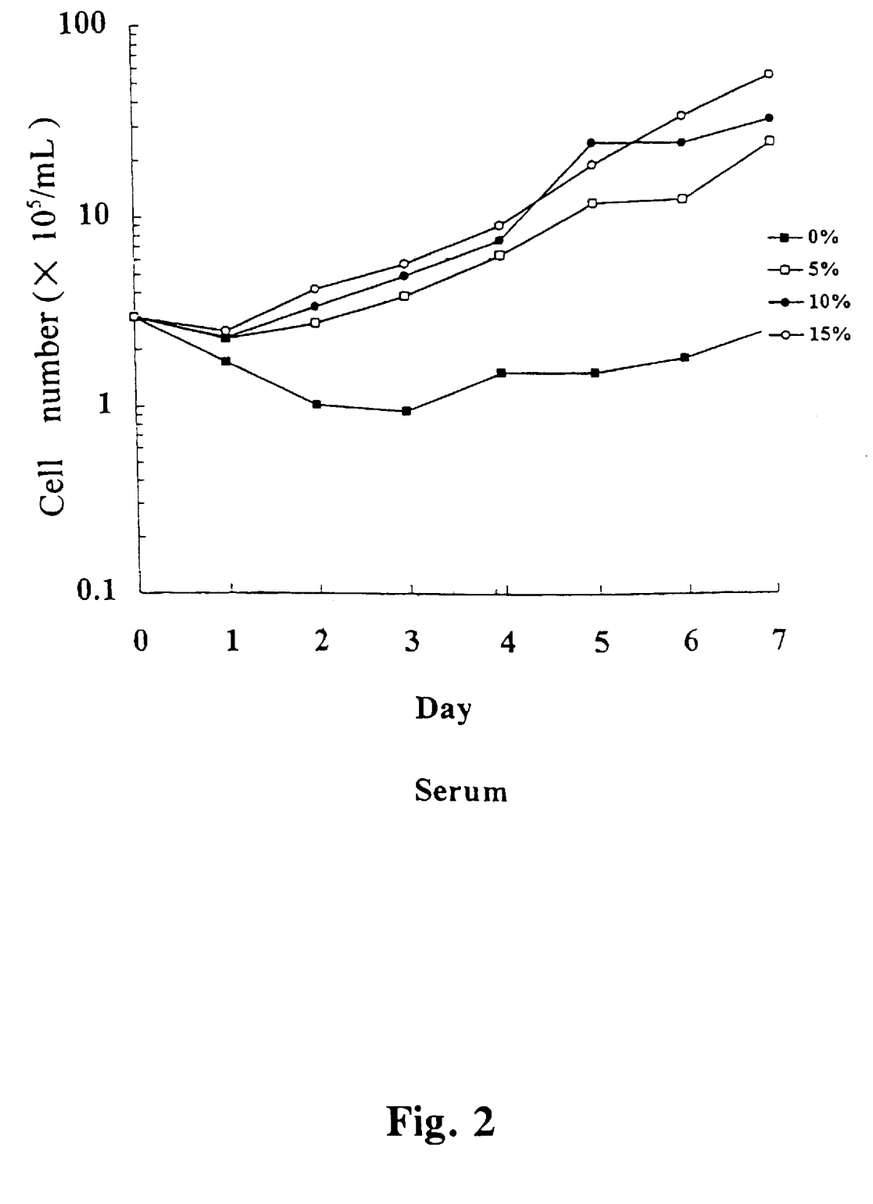
FIG. 2 shows the effects of serum concentrations on the growth rate of PMO cells. PMO cells were cultured in L-15 medium with 0%, 5%, 10%, and 15% serum, respectively, plus NaCl 5 g/L, and glucose 1 g/L. Cell numbers were counted each day.

To study the effects of serum concentrations on the growth of PMO cells, the cells were maintained in L-15 medium at 28° C. with various amounts of fetal calf serum (i.e., 0, 5%, 10%, or 15%). The results of this study are shown in FIG. 2. The results showed that, except for PMO cells grown in L-15 medium without fetal calf serum (which showed a relatively low growth rate), PMO cells in L-15 medium containing 5%, 10%, or 15% fetal calf serum displayed similar growth rates. The doubling times for PMO cell cultures in L-15 medium containing 5%, 10%, and 15% of fetal calf serum were 93 hrs, 83 hrs, and 73 hrs, respectively.

Figure 3:
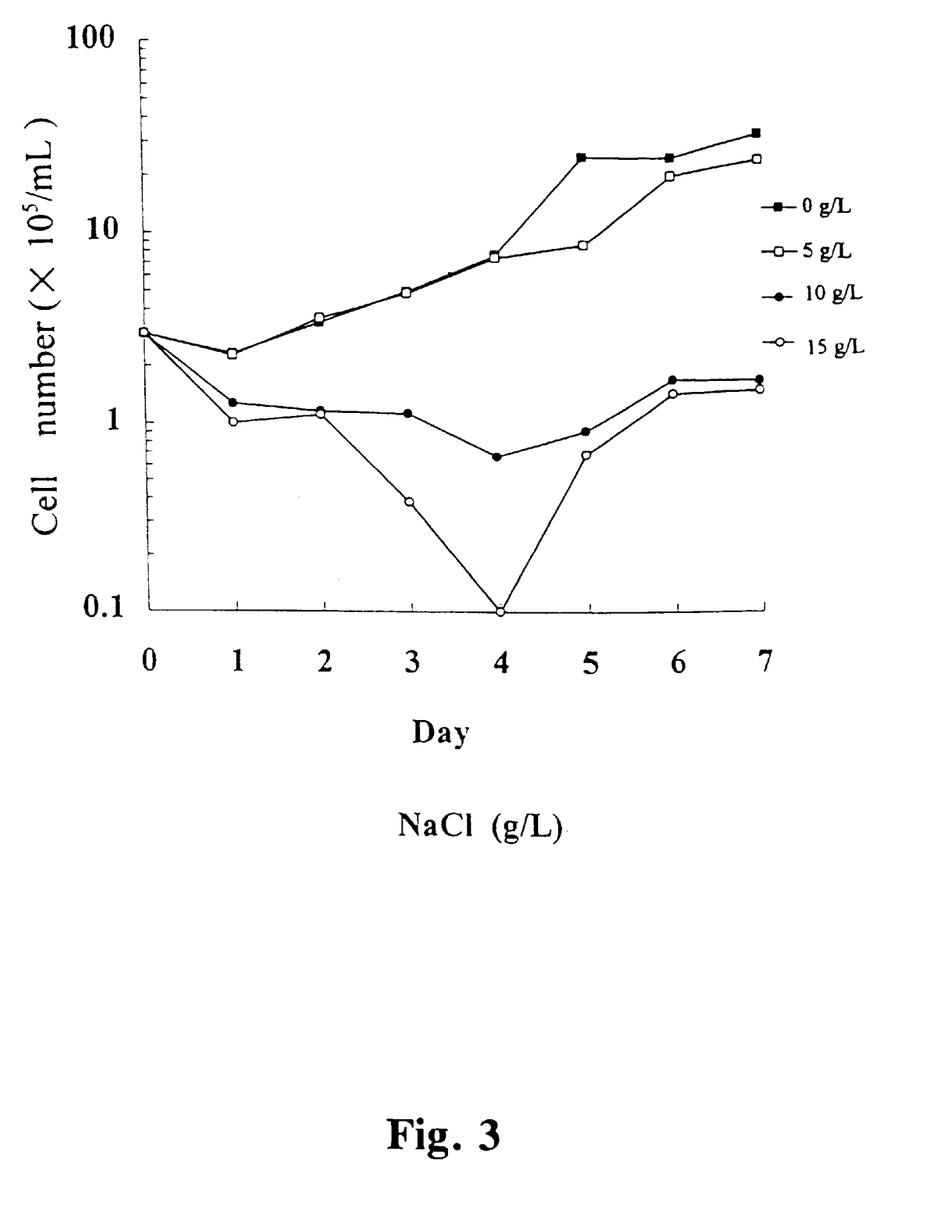
FIG. 3 shows the effects of NaCl concentrations on the growth of PMO cells. PMO cells were cultured in L-15 medium with 0, 5, 10, or 15 g/L NaCl, respectively, plus 10% fetal bovine serum and 1 g/L glucose.

To study the effects of NaCl on PMO cells, various concentrations of NaCl (0 g/L, 5 g/L, 10 g/L, or 15 g/L) were added to PMO cells. The cells were incubated in L-15 medium supplemented with 10% fetal calf serum and 1 g/L glucose at 28° C. As shown in FIG. 3, PMO cells grow well both with (i.e., 5 g/L NaCl) or without NaCl. However, high concentrations of NaCl (i.e., 10 or 15 g/L NaCl) inhibit the cell growth.

Figure 4:
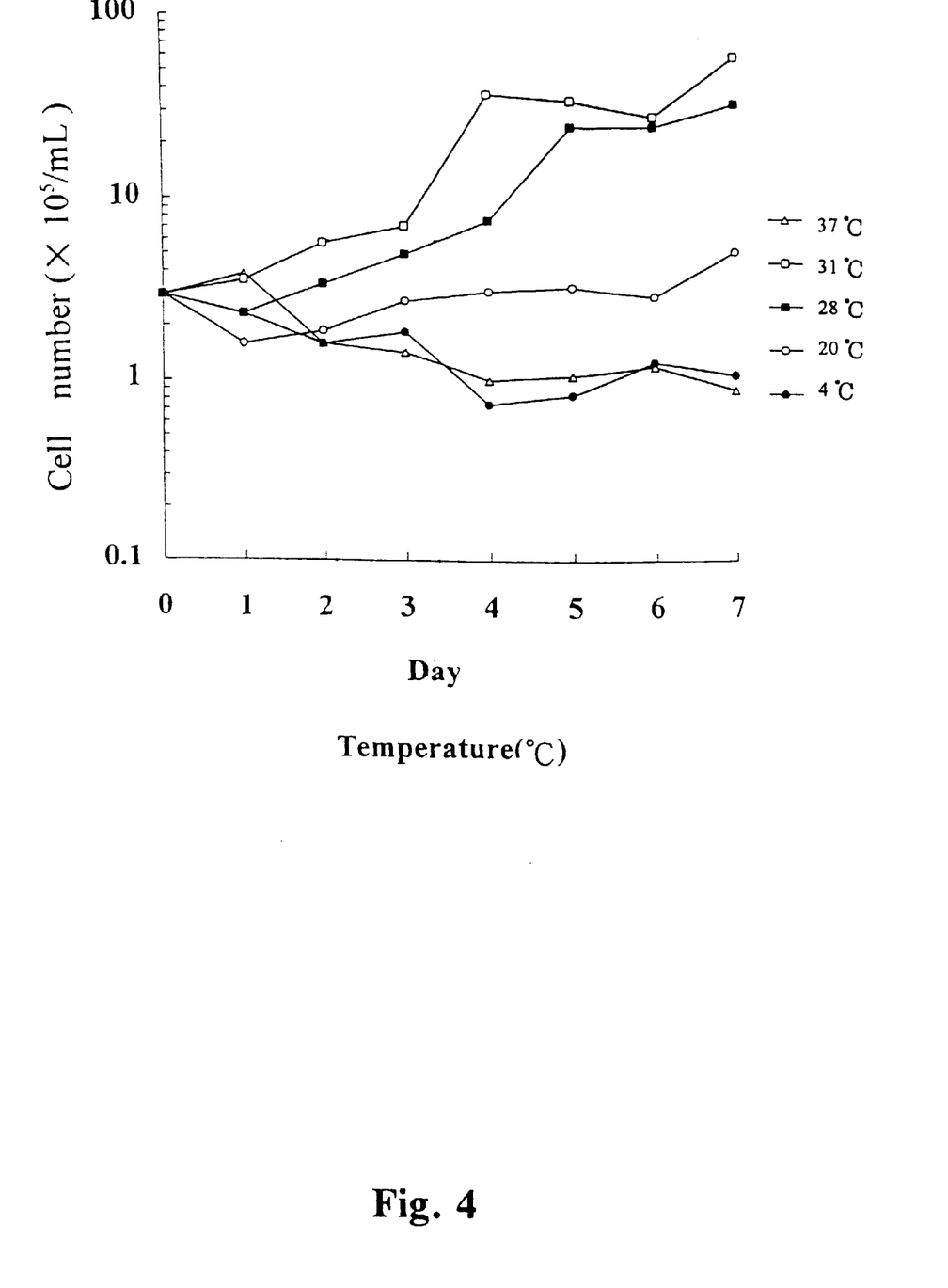
FIG. 4 shows the effects of temperatures on the growth of PMO cells. PMO cells were cultured at 4° C., 20° C., 28° C., 31° C., and 37° C., respectively, in L-15 medium with 10% serum.

To study the effects of temperatures on the growth of PMO cells, the cells were incubated in L-15 medium with 10% serum at various temperatures (0° C., 20° C., 28° C., 31° C., or 37° C.). As shown in FIG. 4, the preferable temperature for PMO cells to grow is 31° C., then follows by 28° C. and 20° C., but not 37° C. or 4° C.

Figure 5:
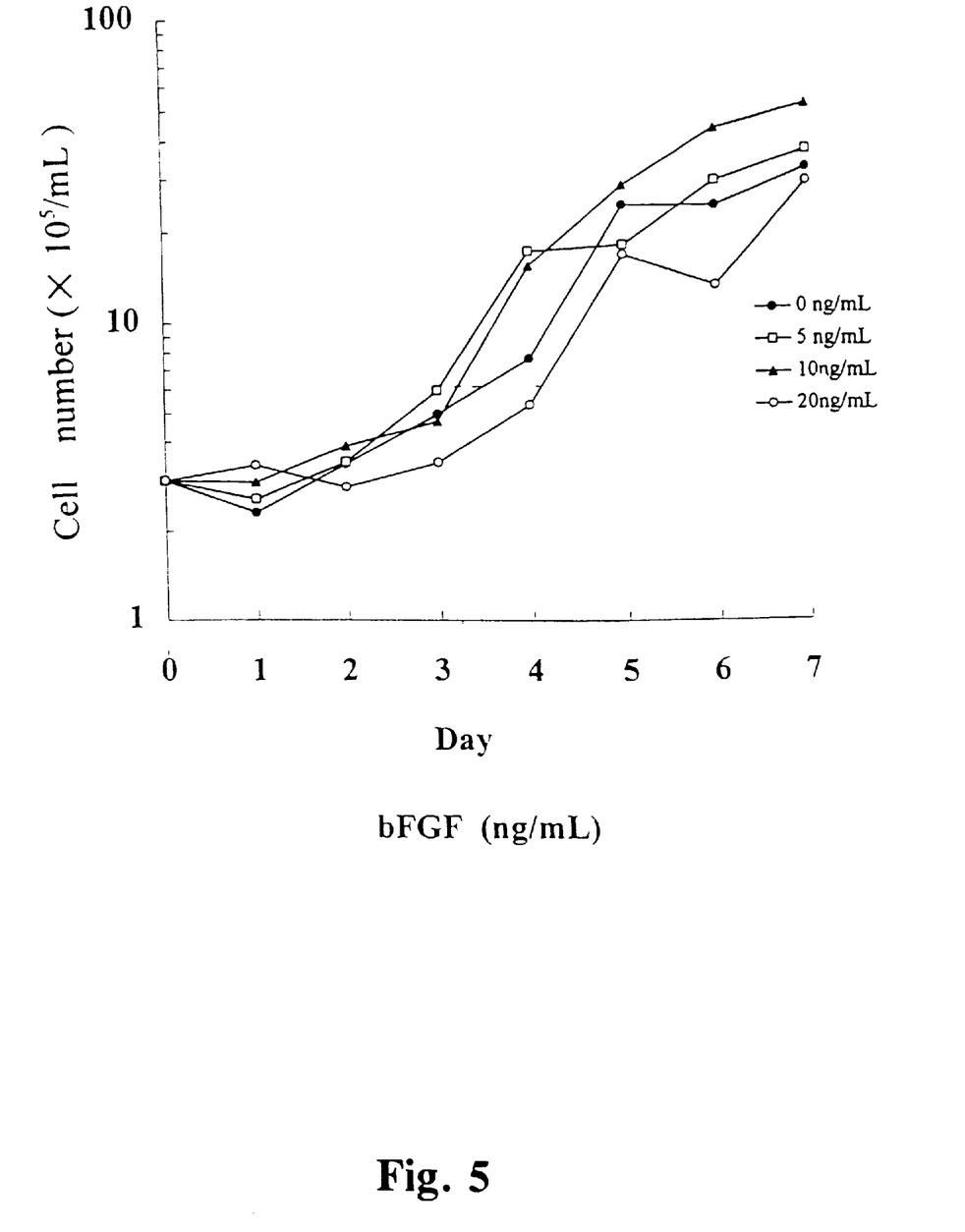
FIG. 5 shows the effects of bFGF concentrations on the growth of PMO cells. PMO cells were cultured in L-15 medium with 10% fetal calf serum, 1 g/L glucose, and 0, 5, 10, or 20 ng/ml of bFGF, respectively.

To study the effects of basic fibroblast growth factor (bFGF), PMO cells were cultured in L-15 medium with 10% fetal calf serum, 1 g/L glucose, and 0, 5, 10 or 20 ng/mL bFGF, respectively. As shown in FIG. 5, the PMO cells grow very well with or without bFGF after passage 12, even though in the initial primary culture, bFGF was required.

EXAMPLE 3
Distribution of the Chromosome Numbers in PMO Cells

The spreading of PMO cell chromosomes was prepared by treating 5 ml of log-phase cultures ($2 \times 10^6$ cells/ml) with 20 μg/ml colchicine in phosphate buffer saline for 4 to 6 hours at 28° C. The cells were dispersed with 0.25% trypsin and centrifuged (900 rpm) for 5 minutes, resuspended for 20 minutes in a hypotonic solution (75 mM KCl) at 37° C., and then fixed in 3:1 methanol:glacial acetic acid for 10 minutes. The fixed cells were dropped vertically onto the slides. After air drying, the cells were stained with Giemsa stain for 2 minutes and the chromosome numbers were counted under a light microscope.

Figure 6:
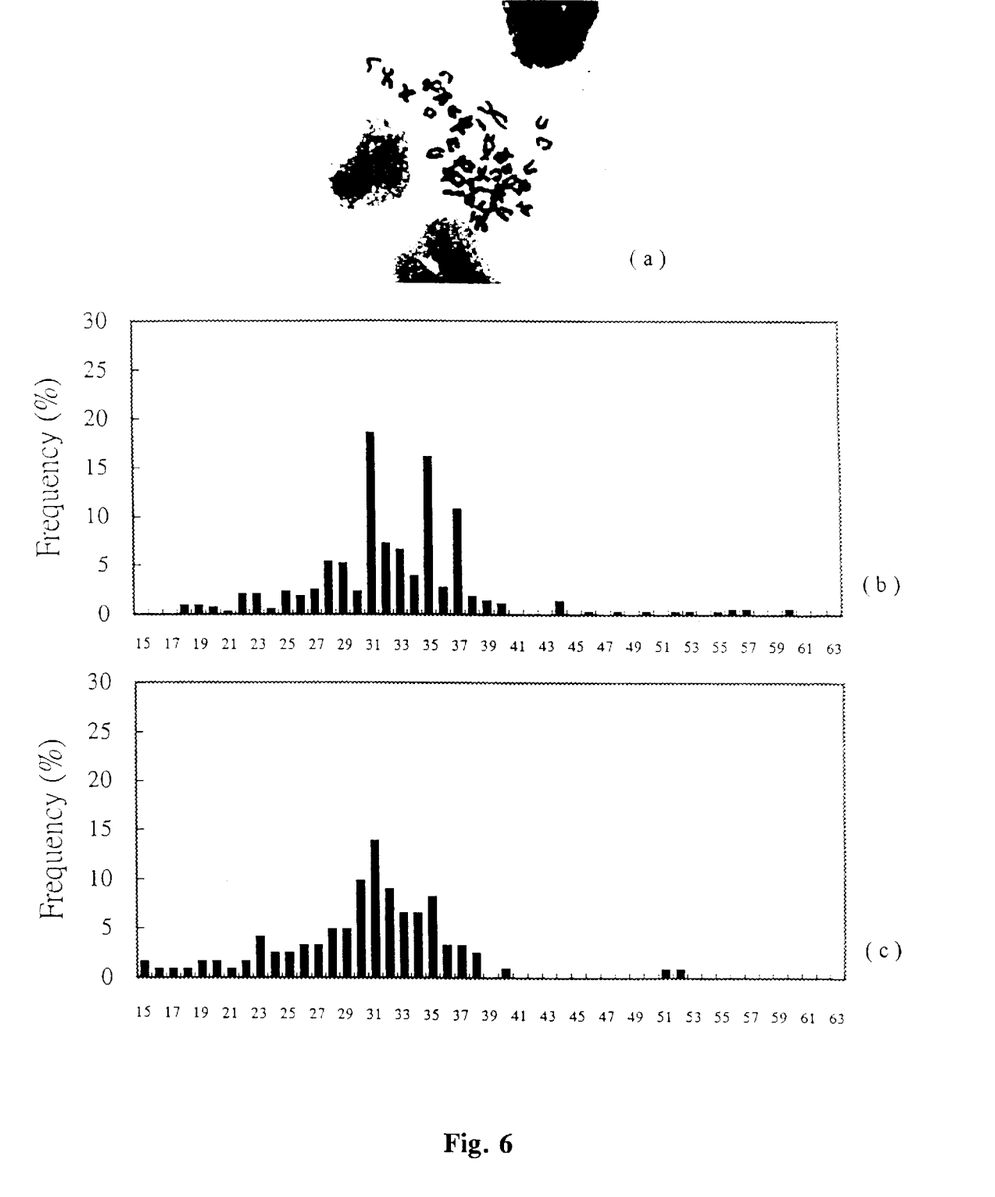
FIGS. 6A, 6B, 6C show the chromosome morphology and chromosome number distribution of PMO cells. A. Chromosome morphology. B. Histogram of chromosome number distribution of PMO cells. C. Histogram of chromosome number distribution of new subculture of Oka organ (PMN).

FIG. 6A shows the chromosome pattern of PMO. As shown in FIG. 6B, the distribution of the chromosome numbers of PMO varies widely (i.e., from 15 to 52), with most of them at 31. As shown in FIG. 6C, the distribution of the chromosome numbers of a new primary culture of P. monodon Oka organ (PMN) shows a similar pattern as that in PMO cell culture, suggesting that PMO cells are derived from P. monodon Oka organ.

The wide range of the distribution of chromosome numbers indicates that transformation occurs during PMO development.

EXAMPLE 4
Identification of PMO as Shrimp Cells by RT-PCR Detection of 18S rRNA Total RNA were purified from fresh shrimp liver and muscle tissues, or from cultured monolayer PMO cells, using RNAzolTM B (TEL-TEST Inc.). 0.1–1 $\mu$g of total RNA and 50 ng of random hexamers in a volume of 11 $\mu$l were denatured at 80° C. for 5 minutes and chilled on ice bath for 2 minutes. Approximately 4 $\mu$l of 5× first round buffer (supplied by the manufacturer), 2 $\mu$l of 0.1 M DTT, 1 $\mu$l of dNTP mix (containing 10 mM of each dNTPs), and 5 units of ribonuclease inhibitor (GIBCO-BRL) were added, and the mixtures were incubated at 42° C. for 2 minutes. Then, 1 $\mu$l (200 units) of SuperScriptTM II reverse transcriptase (GIBCO-BRL) was added, and reverse transcription (RT) reactions were carried out at 42° C. for 1 hour.

For PCR amplification of 18S rRNA, decapods' 18S rRNA specific primer pairs 143F and 145R were used, and the amplification DNA fragment is 848 base pairs in length. Taq DNA polymerase (Promega) was 1:10 diluted with enzyme diluent (Idaho Technology). The total reaction mixture of 10 $\mu$l containing 1 $\mu$l of the RT product, 1× PCR reaction buffer with 2 mM Mg$^{++}$ (Idaho Technology), 1 $\mu$M each of 143F and 145R primers, 200 $\mu$M each of dNTPs, and 1 $\mu$l of diluted Taq DNA polymerase. The mixture was sealed in a 10 $\mu$l capillary tube, and the PCR reaction was performed using a 1605 Air Thermo-cycler (Idaho Technology) under the following conditions: 95° C. denaturation for 3 minutes, followed by 40 cycles of 92° C. denaturation, 60° C. annealing, and 72° C. extension for 1 minute. The PCR products were then electrophoresed on a 1% agarose gel.

Figure 7:
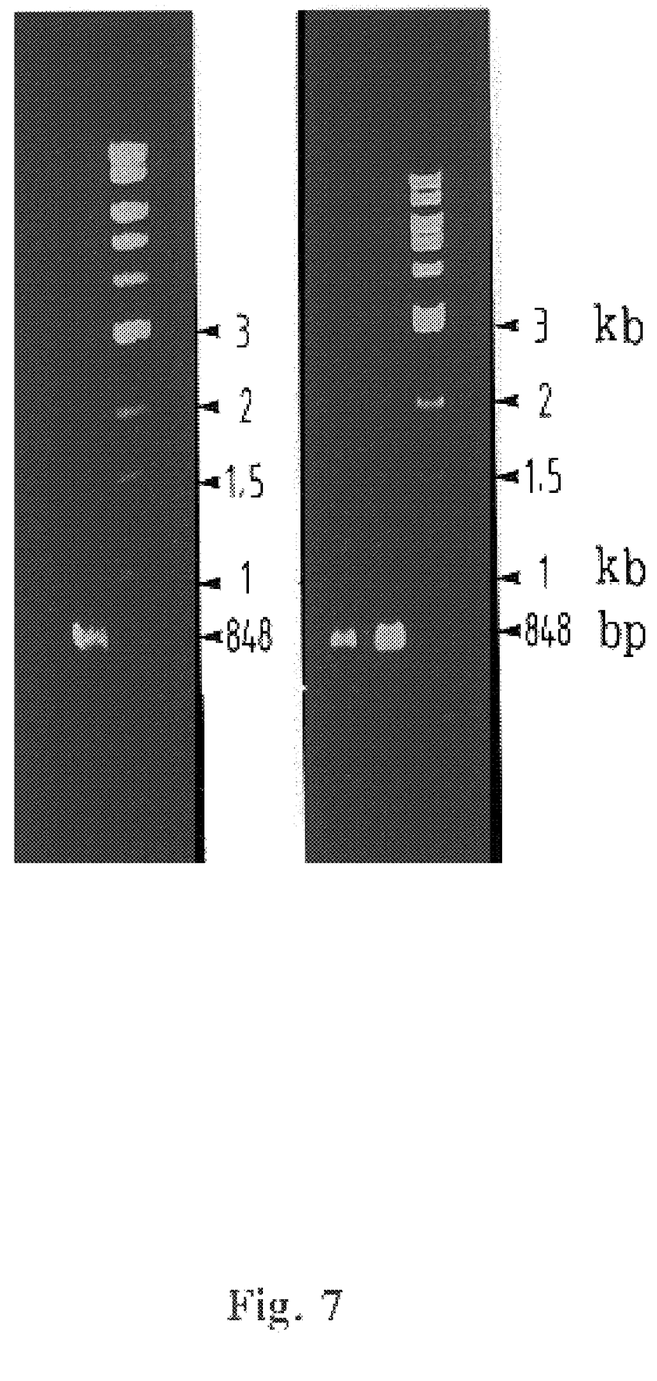
FIG. 7 shows the identification of PMO as shrimp cells by RT-PCR detection of 18S rRNA. Left panel shows a 848 bp RT-PCR product found in PMO cells. Right panel shows a 848 bp PCR product found in liver (left) and muscle (right) of P. monodon shrimp.

As shown in FIG. 7, a 848 bp of RT-PCR product is found in PMO cells (left panel), which matches the 848 bp of RT-PCR product found in the liver and muscle of fresh shrimp (right panel).

The results of the RT-PCR study confirm that PMO cells are derived from shrimp cells.

EXAMPLE 5
Comparisons of the Isozyme Patterns In PMO Cells With P. Monodon. P. Japonica, and Other Fish Cell Lines A comparison of the isozyme patterns of PMO cells, cells from the Oka organ and other organs of P. monodon and P. japonica, and various fish cell lines (RTG-2, and CHSE-214) were conducted using starch gel or polyacrylamide gel electrophoresis.

The samples, which included pelleted cells from cell culture or sliced tissues from shrimp, were sonicated with extraction buffer (pH 7.6) containing 0.1 M Tris, 1 mM EDTA (disodium), 0.05 mM NADP$^+$, and centrifuged for 45 minutes at 4° C. at 17,000× g. The supernatant was loaded onto the starch gel and electrophoresed for 12 hours at 160 V. The gel was sliced horizontally into pieces and each piece was stained for a different isozyme. The starch gel was prepared by adding 51 g starch (11%) in 450 ml TC buffer (pH 8.0) containing 0.135 M Tris and 0.032 M citric acid.

To study the lactate dehydrogenase (LDH) isozyme pattern, the sliced electrophoresed starch gel was first immersed in a solution containing 50 ml of 0.2 M Tris-HCl (pH 8.0) and 8 ml of 1.0 M lithium lactate (pH 8.0), then stained with 1 ml of 10 mg/ml NAD, 1 ml of 5 mg/ml NBT, and 1 ml of 5 mg/ml PMS.

To study the malate dehydrogenase (MDH) isozyme pattern, the sliced electrophoresed starch gel was first immersed in a solution containing 50 ml of 0.2 M Tris-HCl (pH 8.0) and 5 ml of 2.0 M DL-malic acid, then stained with 1 ml of 10 mg/ml NAD, 1 ml of 5 mg/ml NBT, and 1 ml of 5 mg/ml PMS.

To study the esterase isozyme pattern, the cell extracts were loaded onto a 7.5% polyacrylamide gel and electrophoresed at 175 V for 2 hours and 17 minutes, 350 V for 1 hr, 400 V for 47 minutes, and 500 V for 5 minutes. Then the gel was stained with 3 ml of 1% ($\alpha$ or $\beta$) naphthyl acetate solution (naphthyl in 50% acetone), then mixed with 50 ml of 0.2 M Tris-HCl (pH 7.0), and 0.05 g of fast blue BB for 30 minutes to 2 hours at 37° C.

Figure 8:
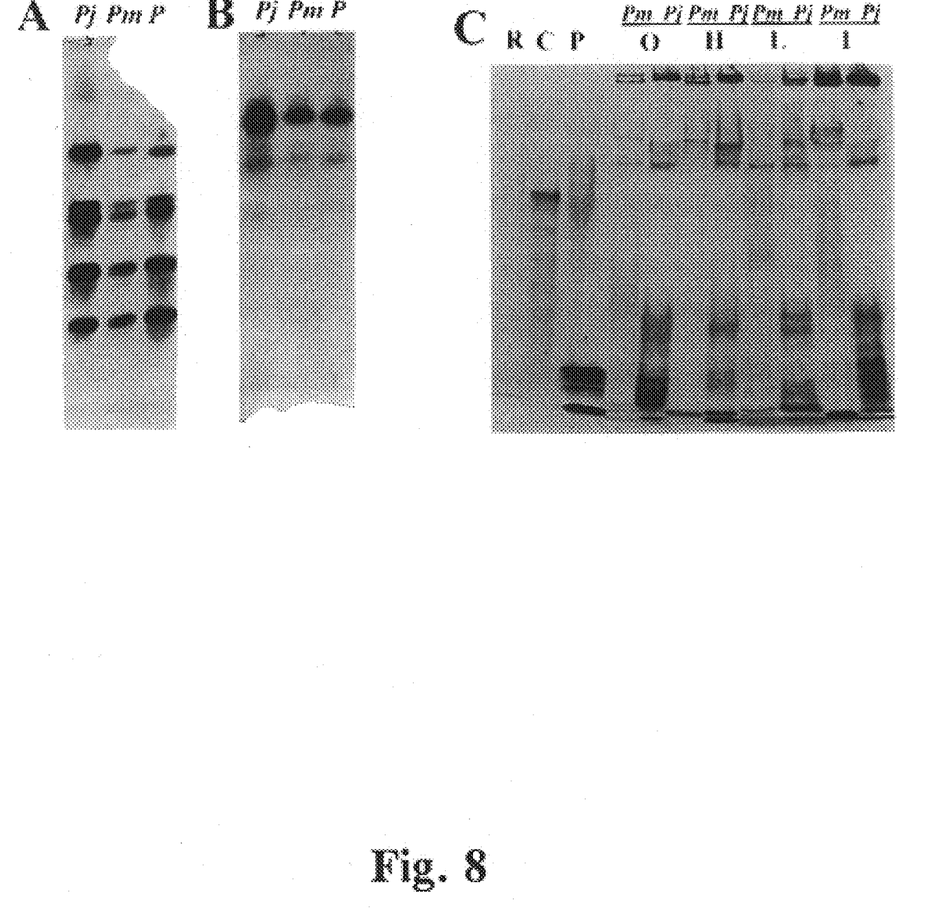
FIGS. 8A, 8B, 8C is a comparison of different isozyme patterns of PMO cells and the Oka organs of P. monodon, P. japonica, and fish cell lines. A. Lactate dehydrogenase (LDH) isozyme patterns of PMO (P) cells, and the Oka organs of P. monodon (Pm) and P. japonica (Pj). B. Malate dehydrogenase (MDH) isozyme patterns of PMO (P) cells, and the Oka organs of P. monodon (Pm) and P. japonica (Pj). C. Esterase isozyme patterns of PMO (P) cells, RTG-2 cells (R), and CHSE-214 cells (C), and the Oka organs (O), hearts (H), lungs (L), and intestines (I) of P. monodon (Pm) and P. japonica (Pj).

As shown in FIG. 8, the LDH isozyme pattern in PMO cells is the same as that in P. monodon as well as in P. japonica (FIG. 8A). However, the MDH in PMO cells is the same as that of P. monodon but different from that of P. japonica (FIG. 8B). In addition, as shown in FIG. 8C, the esterase isozyme pattern of PMO cells differs from the Oka organ of P. monodon, and fish cell lines-RTG-2 and CHSE-214 cells. Furthermore, the esterase isozyme patterns of the Oka organ, heart, lung, and intestine of P. monodon are different from those of P. japonica, respectively.

The LDH and MDH isozyme patterns of PMO indicate that PMO cells are related to the Oka organ of P. monodon. The conflicting results derived from the esterase isozyme studies, which show that the esterase isozyme pattern of PMO is different not only from other fish cells (e.g., RTG-2 and CHSE-214 cells), but also from the Oka organ, heart, lung, and intestine of P. monodon and P. japonica, nevertheless, confirm that PMO cells become transformed cells.

In accordance with the second embodiment of the present invention, there is provided for an in vitro culture system for growing virus, particularly, but not limited to, shrimp virus, in PMO cells, so that future evaluation of the biological, biochemical, and serological characteristics of the virus can be carried on. The experimental designs and results are illustrated, but not limited to, in the following examples:

EXAMPLE 6
Viral Susceptibility of PMO Cells

The following viruses were used to test the viral susceptibility of PMO cells: IPNV (infectious pancreatic necrosis virus), IHNV (infectious hematopoietic necrosis virus), WSSV (white spot syndrome virus), CAV (clam aquareovirus), IHHNV (infectious Hypodermal and Hematopoietic Necrosis Virus), and MBV (monodon baculovirus).

In particular, WSSV and MBV were collected and purified as follows:

For WSSV, the virus was collected from moribund penaeid shrimp (Penaeus monodon) in shrimp farms located in the Southern part of Taiwan. The purification of WSSV was carried out as follows: The Oka organ and exoskeleton with underlying epidermis and hepatopancreas from 10 frozen shrimp were homogenized with 25 ml of TNE cold extraction buffer (0.2 M Tris-HCl, 0.4 M NaCl, and 1 mM EDTA) by polytron (Kinamatica, PT10/35) and centrifuged at 1,000× g for 10 minutes. The suspension was collected and purified by linear 35 to 70% (W/W) sucrose gradient centrifugation at 100,000× g (Hitachi SRP 40 Ti rotor at 30,000 rpm) for 1 hour. The visible viral band in the middle of the gradient was removed and pelleted by centrifugation at 100,000× g at 4° C. for 1 hour. The pellet was washed twice with cold TE buffer (0.2 M Tris-HCl, and 1 mM EDTA), resuspended with 0.5 ml cold TE buffer, and stored at −20° C.

For MBV (Penaeus monodon baculovirus), MBV virions were prepared as follows: Samples were examined by phase or bright field microscopy to search for occulsion bodies. After squashing the shrimp tissue, MBV occlusion bodies could be identified by staining the squashed tissue with 1% Eosin solution. The virus was then isolated by homogenizing the shrimp tissue in cold TNE buffer on ice using a polytron. The homogenized solution was centrifuged for 10 minutes at 1,000× g to remove any cell debris. The supernatant was then layered onto a 36–65% (W/W) sucrose gradient and centrifuged for 60 minutes at 100,000× g. The visible viral band in the middle of the gradient was removed, diluted twice with TE buffer, and pelleted by centrifugation for 1 hour at 100,000× g. The pellet was resuspended with 0.5 ml of cold TE buffer and stored at −20° C.

Viral susceptibility can be determined by examining the cells under light microscope for cytopathic effect (CPE).

A comparative study of the viral susceptibility between PMO and CHSE-214 cells is shown in Table 1:

TABLE 1

Viral Susceptibility in PMO and CHSE-214 Cells

|  | CHSE-214 ($TCID_{50}$/ml) | PHO ($TCID_{50}$/ml) |
| --- | --- | --- |
| IPNV | $2.0 \times 10^7$ | $6.6 \times 10^6$ |
| IHNV | $5.5 \times 10^6$ | 0 |
| WSSV | 0 | $3.5 \times 10^6$ |
| CAV | $2.7 \times 10^8$ | 0 |
| IHHNV | 0 | $1 \times 10^5$ |
| MBV | 0 | $1 \times 10^{3-4}$* |

IPNV: infectious pancreatic necrosis virus;
IHNV: infectious hematopoietic necrosis virus;
WSSV: white spot syndrome virus;
CAV: clam aquareovirus;
IHHNV: infectious hypodermal and hematopoietic necrosis virus;
MBV: Penaeus monodon baculovirus;
CHSE-214: chinook salmon embryo cells;
PMO: Oka organ cells of Panaeus monodon;
*: viral susceptibility also confirmed by electron microscopic pictures;
$TCID_{50}$/ml: 50% tissue culture infectious dose and point.

As shown in Table 1, IPNV (fish and shellfish virus) replicates in CHSE-214 and PMO cells with the titer of $2 \times 10^7$ $TCID_{50}$/ml and $6.6 \times 10^6$ $TCID_{50}$/ml, respectively. IHNV (fish virus) and CAV (shellfish virus) replicates in CHSE-214 cells, but not in PMO. WSSV and IHHNV replicate in PMO cells at $3.5 \times 10^6$ $TCID_{50}$/ml and $1 \times 10^5$ $TCID_{50}$/ml, respectively, but not in CHSE-214 cells. These two shrimp viruses were consecutively passed in PMO cells with the least virus titers. After 4 passages, WSSV and IHHNV remained at about $10^{5-6}$ $TCID_{50}$/ml. MBV also replicated in PMO cells, as evident by $10^{3-4}$ $TCID_{50}$/ml and by electron microscopy.

The results of the viral susceptibility study, which show that PMO cells are susceptible to WSSV, IHHNV, MBV, and IPNV, but not IHNV and CAV, suggest that there is host specificity among penaeid baculoviruses. Also, the CPE shown by infecting WSSV, IHHNV, or MBV in PMO cells was not induced by cytotoxicity. Rather, it was truly CPE because the CPE appeared after 4 to 5 passages, and each passage reached about $10^5$ TCID/ml where the most diluted virus suspension was used for next titration. The results of the viral susceptibility study also confirmed that IPNV has the ability to infect shrimp.

EXAMPLE 7

Subcloning of PMO Cells

The monolayer cells of PMO in T25 flask were trypsinized for minutes to form a single cell suspension. Then, 1 to 5 μl of the single cell suspension was taken into an eppendorf ring, which was in a tissue culture petri dish, and incubated at 28° C. until the cell morphology appeared. The eppendorf ring was then taken off, and the non-target cells were scrape off by a scraper so that only the target cells were left on the petri dish.

Figure 9:
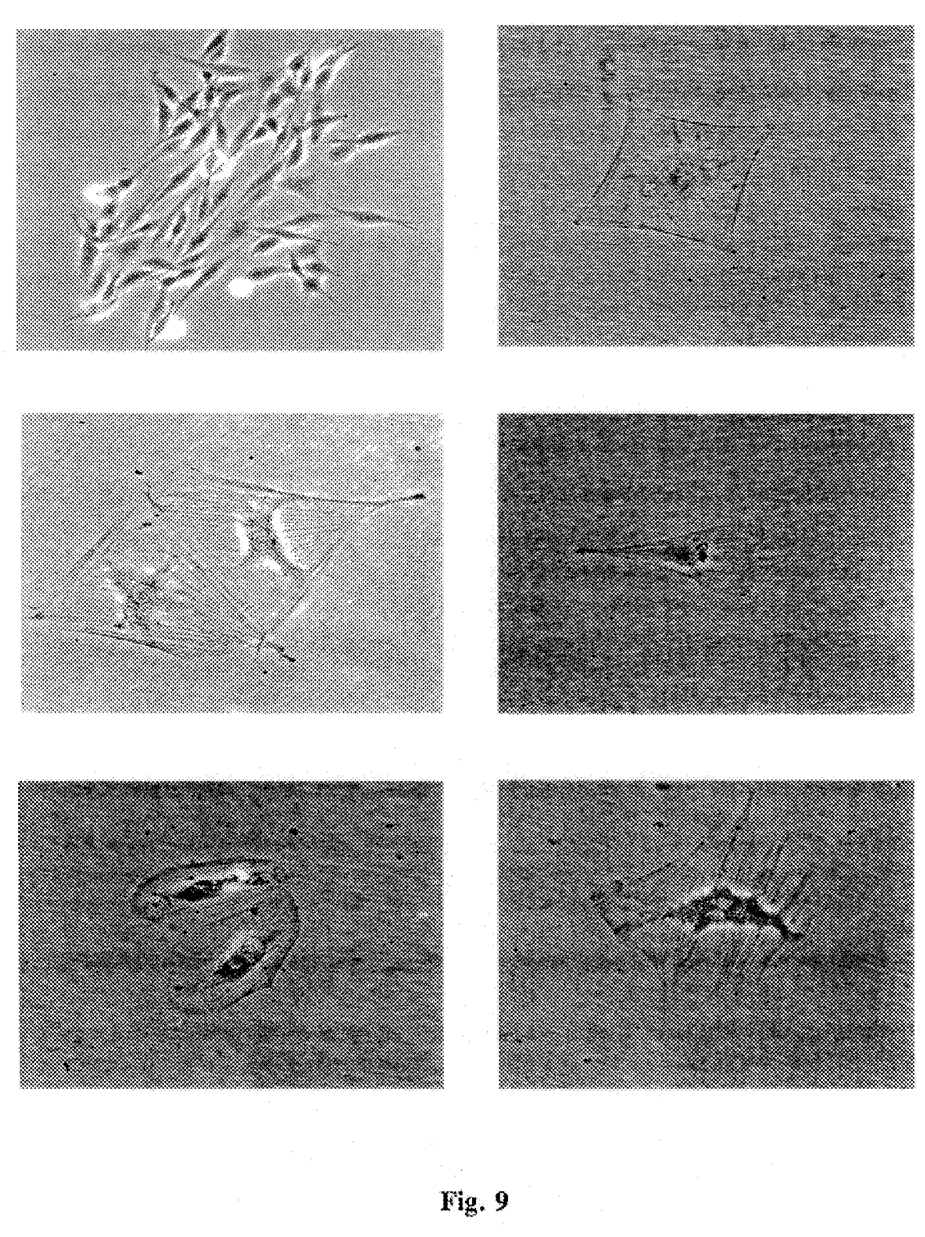
FIG. 9 shows the morphology of PMO cells. Six different morphological shapes of PMO cells were found, which represent irregular, round, fan shape, triangle, square and fibroblast cells, respectively.

As shown in FIG. 9, the subcloning of PMO results in findings of six different morphologies of cells in PMO, which demonstrate irregular, round, fan, triangle, square shaped cell with concave sides, and fibroblast cells. These subclones varied in viral susceptibility, probably because they contain different viral receptors. To get higher viral replication in PMO cells, using a subclone of PMO which demonstrates higher viral susceptibility is highly recommended.

EXAMPLE 8

Mass Production of Virus From PMO

Typically, mass production of virus from an infected cell line requires that the infectivity titres be at least $10^8$ to $10^9$ $TCID_{50}$/ml, which can be achieved by serial passages of purified virus into the cells. In the present case, the infectivity titres can be increased not only by serial passages of the purified virus into PMO cells, but also by selecting the PMO subclones which demonstrate the highest susceptibility.

After collecting the virus-produced plaques, the cells can be homogenized in TNE cold extraction buffer (0.2 M Tris-HCl, 0.4 M NaCl, and 1 mM EDTA) by polytron (Kinamatica, PT10/35) and centrifuged at 1,000× g for 10 minutes. The virus purification method was the same as the methods of purifying WSSV and MBV described in the previous section (Supra).

Although the foregoing invention has been described in some detail by way of illustration and example for purposes of clarity of understanding, it will be obvious that certain changes and modifications may be practiced within the scope of the appended claims.

What is claimed is:

1. An immortal cell line PMO which is CCTCC deposit No. C 200004, whereby said cell line is isolated from Penaeus monodon oka organ.

2. A method for propagating a virus comprising the steps of:

adding a stock of said virus to the immortal cell line PMO of claim 1;

incubating the immortal cell line in a nutrient medium; and harvesting said virus.

3. The method for propagating a virus according to claim 2, wherein said virus comprises one which is selected from the group consisting of white spot syndrome virus (WSSV), Penaeus monodon baculovirus (MBV), infectious hypodermal and hematopoietic necrosis virus (IHHNV), and infectious pancreatic necrosis virus (IPNV).

4. The method for propagating a virus according to claim 2, wherein said nutrient medium comprises Leibovitz's L-15 medium supplemented with fetal calf serum.

5. The method for producing a virus according to claim 2, wherein said harvesting comprises the steps of:

forming a virus-containing cell homogenate in a buffer;

centrifuging said cell homogenate and collecting a supernatant;

layering said supernatant on a gradient;

centrifuging said gradient till an isopycnic condition is reached; and collecting said virus from a visible viral band in said isopycnic gradient.

* * * * *